US011154466B2

(12) United States Patent
Gawtrey et al.

(10) Patent No.: US 11,154,466 B2
(45) Date of Patent: *Oct. 26, 2021

(54) AEROSOL DEVICE BASED ON A CALCIUM SALT, ON A FIXING POLYMER, ON A SURFACTANT AND ON WATER

(71) Applicant: L'OREAL, Paris (FR)

(72) Inventors: Jonathan Gawtrey, Boulogne (FR); Dorothée Pasquet, Bois-Colombes (FR)

(73) Assignee: L'OREAL, Paris (FR)

( * ) Notice: Subject to any disclaimer, the term of this patent is extended or adjusted under 35 U.S.C. 154(b) by 538 days.

This patent is subject to a terminal disclaimer.

(21) Appl. No.: 15/322,771

(22) PCT Filed: Jun. 30, 2015

(86) PCT No.: PCT/EP2015/064780
§ 371 (c)(1),
(2) Date: Dec. 29, 2016

(87) PCT Pub. No.: WO2016/001190
PCT Pub. Date: Jan. 7, 2016

(65) Prior Publication Data
US 2018/0200161 A1 Jul. 19, 2018

(30) Foreign Application Priority Data
Jun. 30, 2014 (FR) .................................... 1456128

(51) Int. Cl.
A61Q 5/06 (2006.01)
A61K 8/04 (2006.01)
A61K 8/41 (2006.01)
A61K 8/46 (2006.01)
A61K 8/81 (2006.01)
A61K 8/19 (2006.01)
A61K 8/39 (2006.01)
A61K 8/44 (2006.01)
A61K 8/55 (2006.01)
A61K 8/73 (2006.01)

(52) U.S. Cl.
CPC .............. A61K 8/046 (2013.01); A61K 8/19 (2013.01); A61K 8/39 (2013.01); A61K 8/416 (2013.01); A61K 8/44 (2013.01); A61K 8/442 (2013.01); A61K 8/46 (2013.01); A61K 8/463 (2013.01); A61K 8/556 (2013.01); A61K 8/73 (2013.01); A61K 8/731 (2013.01); A61K 8/817 (2013.01); A61K 8/8141 (2013.01); A61K 8/8147 (2013.01); A61K 8/8158 (2013.01); A61K 8/8182 (2013.01); A61K 8/8194 (2013.01); A61Q 5/06 (2013.01); A61K 2800/412 (2013.01)

(58) Field of Classification Search
None
See application file for complete search history.

(56) References Cited

U.S. PATENT DOCUMENTS

| 2,047,398 A | 7/1936 | Voss et al. |
| 2,102,113 A | 12/1937 | Djordjevitch |
| 2,723,248 A | 11/1955 | Wright |
| 3,161,460 A | 12/1964 | Huber |
| 3,504,862 A | 4/1970 | Lowry |
| 3,579,629 A | 5/1971 | Pasero et al. |
| 3,589,978 A | 6/1971 | Kamal et al. |
| 3,628,733 A | 12/1971 | Kahn |
| 3,716,633 A | 2/1973 | Viout et al. |
| 3,767,125 A | 10/1973 | Gehres et al. |
| 3,792,068 A | 2/1974 | Luedders et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,180 A | 1/1979 | Naik et al. |
| 4,137,208 A | 1/1979 | Elliott |

(Continued)

FOREIGN PATENT DOCUMENTS

DE 2330956 A1 1/1974
DE 10 2005 025 016 A1 12/2005

(Continued)

OTHER PUBLICATIONS

Non-Final Office Action for co-pending U.S. Appl. No. 14/787,983, dated Jun. 26, 2019.

(Continued)

Primary Examiner — Jyothsna A Venkat
(74) Attorney, Agent, or Firm — The Marbury Law Group, PLLC

(57) ABSTRACT

The invention relates to an aerosol device which contains a composition comprising: (i) one or more water-insoluble calcium salts, (ii) one or more fixing polymers, (iii) one or more surfactants, (iv) water, and (v) less than 20% by weight, relative to the total weight of the composition, of one or more propellants. It also relates to a process for shaping the hair and/or retaining the hairstyle, using the aerosol device of the invention.

13 Claims, No Drawings

(56) References Cited

U.S. PATENT DOCUMENTS

| | | |
|---|---|---|
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,401,271 A | 8/1983 | Hansen |
| 4,450,151 A | 5/1984 | Shinozawa |
| 4,557,916 A | 12/1985 | Witham |
| 4,605,553 A | 8/1986 | Passalacqua |
| 4,693,925 A | 9/1987 | Cheung et al. |
| 4,728,571 A | 3/1988 | Clemens et al. |
| 4,822,596 A | 4/1989 | Callingham et al. |
| 4,871,529 A | 10/1989 | Sramek |
| 4,874,554 A | 10/1989 | Lange et al. |
| 4,957,732 A | 9/1990 | Grollier et al. |
| 4,972,037 A | 11/1990 | Garbe et al. |
| 4,983,377 A | 1/1991 | Murphy et al. |
| 5,297,739 A | 3/1994 | Allen |
| 5,300,284 A | 4/1994 | Wiechers et al. |
| 5,508,259 A | 4/1996 | Holzner et al. |
| 5,538,717 A | 7/1996 | La Poterie |
| 5,614,173 A | 3/1997 | Ulmer et al. |
| 5,643,557 A | 7/1997 | Eteve et al. |
| 5,690,924 A | 11/1997 | Keil et al. |
| 5,879,669 A | 3/1999 | Clausen et al. |
| 5,900,241 A | 5/1999 | Roulier et al. |
| 6,106,813 A | 8/2000 | Mondet et al. |
| 6,166,093 A | 12/2000 | Mougin et al. |
| 6,210,689 B1 | 4/2001 | Martino et al. |
| 6,245,324 B1 | 6/2001 | Hough et al. |
| 6,319,959 B1 | 11/2001 | Mougin et al. |
| 6,350,434 B1 | 2/2002 | Bhatt et al. |
| 6,372,876 B1 | 4/2002 | Kim et al. |
| 6,395,265 B1 | 5/2002 | Mougin et al. |
| 6,415,992 B1 | 7/2002 | Blondeel et al. |
| 6,589,509 B2 * | 7/2003 | Keller ................ A61K 8/03 424/45 |
| 6,592,854 B1 | 7/2003 | Dupuis |
| 6,751,886 B2 | 6/2004 | Chang et al. |
| 7,063,834 B2 | 6/2006 | Mougin et al. |
| 7,585,824 B2 | 9/2009 | Popplewell et al. |
| 10,440,140 B2 | 10/2019 | Barraclough et al. |
| 10,532,880 B2 * | 1/2020 | Smail ................ A61K 8/8147 |
| 2002/0017575 A1 | 2/2002 | Andrews et al. |
| 2002/0031478 A1 | 3/2002 | Keller et al. |
| 2002/0150546 A1 | 10/2002 | Mougin et al. |
| 2003/0150624 A1 | 8/2003 | Rummel |
| 2003/0150937 A1 | 8/2003 | Laidler et al. |
| 2003/0163878 A1 | 9/2003 | Pruche |
| 2003/0185777 A1 | 10/2003 | Banowski et al. |
| 2003/0191271 A1 | 10/2003 | Mondet et al. |
| 2004/0047812 A1 | 3/2004 | Pataut et al. |
| 2004/0170575 A1 | 9/2004 | Belli et al. |
| 2004/0175404 A1 | 9/2004 | Shefer et al. |
| 2005/0163737 A1 | 7/2005 | Lemoine et al. |
| 2005/0220723 A1 | 10/2005 | Benabdillah et al. |
| 2005/0224524 A1 | 10/2005 | Khan et al. |
| 2008/0019928 A1 | 1/2008 | Franzke et al. |
| 2008/0172807 A1 | 7/2008 | Brun |
| 2008/0274071 A1 | 11/2008 | Kaplan et al. |
| 2009/0061004 A1 | 3/2009 | Birkel et al. |
| 2009/0218418 A1 | 9/2009 | Sharief |
| 2010/0040572 A1 | 2/2010 | Mougin |
| 2012/0097180 A1 | 4/2012 | Harris et al. |
| 2012/0171264 A1 | 7/2012 | Bernet et al. |
| 2012/0258052 A1 | 10/2012 | Mueller et al. |
| 2012/0282190 A1 | 11/2012 | Hammer |
| 2013/0289080 A1 | 10/2013 | Masse et al. |
| 2013/0340786 A1 * | 12/2013 | Rodrigues ............ A61K 8/046 132/210 |
| 2014/0030196 A1 | 1/2014 | Russell et al. |
| 2014/0079747 A1 | 3/2014 | Dihora et al. |
| 2015/0014443 A1 | 1/2015 | Albisetti |
| 2015/0041559 A1 | 2/2015 | Albisetti |
| 2015/0104397 A1 | 4/2015 | Smail et al. |
| 2015/0139917 A1 | 5/2015 | Gawtrey et al. |
| 2016/0075501 A1 | 3/2016 | Aubert et al. |
| 2016/0100667 A1 | 4/2016 | Aubert et al. |
| 2016/0106634 A1 | 4/2016 | Gawtrey et al. |
| 2018/0000700 A1 | 1/2018 | Smail et al. |
| 2018/0016087 A1 | 1/2018 | Smail et al. |
| 2018/0243763 A1 | 8/2018 | Eurippini |

FOREIGN PATENT DOCUMENTS

| | | |
|---|---|---|
| DE | 102008035013 A1 | 1/2010 |
| EP | 0080976 A1 | 6/1983 |
| EP | 0095238 A2 | 11/1983 |
| EP | 0186507 A2 | 7/1986 |
| EP | 0342834 A2 | 11/1989 |
| EP | 0412704 A2 | 2/1991 |
| EP | 0412707 A1 | 2/1991 |
| EP | 0452208 A1 | 10/1991 |
| EP | 0530974 A1 | 3/1993 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0751162 A1 | 1/1997 |
| EP | 0 974332 A1 | 1/2000 |
| EP | 1026220 A1 | 8/2000 |
| EP | 1407754 A1 | 4/2004 |
| EP | 2444160 A1 | 4/2012 |
| EP | 2777770 A1 | 9/2014 |
| FR | 1222944 A | 6/1960 |
| FR | 1400366 A | 5/1965 |
| FR | 1564110 A | 4/1969 |
| FR | 1578989 A | 8/1969 |
| FR | 1580545 A | 9/1969 |
| FR | 1600138 A | 7/1970 |
| FR | 2077143 A | 10/1971 |
| FR | 2199719 A1 | 4/1974 |
| FR | 2265781 A1 | 10/1975 |
| FR | 2265782 A1 | 10/1975 |
| FR | 2350384 A1 | 12/1977 |
| FR | 2357241 A1 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004901 A1 | 10/2014 |
| FR | 3004902 A1 | 10/2014 |
| FR | 3004929 A1 | 10/2014 |
| FR | 3031437 A1 | 7/2016 |
| GB | 839805 A | 6/1960 |
| GB | 922457 A | 4/1963 |
| GB | 1021400 A | 3/1966 |
| GB | 1218222 A | 1/1971 |
| GB | 1235908 A | 6/1971 |
| GB | 1331819 A | 9/1973 |
| GB | 1408388 A | 10/1975 |
| GB | 1572626 A | 7/1980 |
| GB | 2340891 A | 3/2000 |
| JP | 2003-326197 A | 11/2003 |
| JP | 2011-213619 A | 10/2011 |
| LU | 75370 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |
| WO | 02/078653 A1 | 10/2002 |
| WO | 02/096379 A1 | 12/2002 |
| WO | 03/045573 A1 | 6/2003 |
| WO | 03/049711 A2 | 6/2003 |
| WO | 2004/043608 A1 | 5/2004 |

(56) References Cited

FOREIGN PATENT DOCUMENTS

| | | | |
|---|---|---|---|
| WO | 2011/019539 A2 | 2/2011 |
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177647 A1 | 11/2014 |
| WO | 2014/177649 A1 | 11/2014 |
| WO | 2016/092109 A1 | 6/2016 |
| WO | 2018/162701 A1 | 9/2018 |
| WO | 2018/162707 A1 | 9/2018 |
| WO | 2018/162711 A1 | 9/2018 |

OTHER PUBLICATIONS

Non-Final Office Action for co-pending U.S. Appl. No. 14/888,013, dated Mar. 14, 2019.
Mintel: "Clean Freak Refreshing Dry Shampoo," XP007923188, Demert Brands, Mar. 2014.
Final Office Action for co-pending U.S. Appl. No. 14/399,764, dated Jun. 7, 2019.
Notice of Allowance for co-pending U.S. Appl. No. 15/523,242, dated Jun. 12, 2019.
Final Office Action for co-pending U.S. Appl. No. 15/541,741, dated Jul. 11, 2019.
Non-Final Office Action for co-pending U.S. Appl. No. 15/541,741, dated Mar. 3, 2020.
CLEARCO, "Cyclo-1400-DM D5 Cyclomethicone/dimethicone blend," ([retrieved from on-line website: http://www.clearcoproducts.com/cyclo-1400-d5-blend.html], 2013, pp. 1-2.
Wayback Machine to support publication year of CLEARCO (Year: 2013).
Notice of Allowance for co-pending U.S. Appl. No. 15/541,738, dated Sep. 4, 2019.
Supplemental Notice of Allowance for co-pending U.S. Appl. No. 15/523,242, dated Sep. 5, 2019.
Non-Final Office Action for co-pending U.S. Appl. No. 15/324,804, dated Oct. 10, 2019.
Final Office Action for co-pending U.S. Appl. No. 14/888,013, dated Oct. 18, 2019.
Non-Final Office Action for co-pending U.S. Appl. No. 14/888,002, dated Oct. 7, 2019.
Non-Final Office Action for co-pending U.S. Appl. No. 15/541,743, dated Nov. 21, 2019.
Non-Final Office Action for co-pending U.S. Appl. No. 15/523,232, dated Feb. 20, 2020.
Final Office Action for co-pending U.S. Appl. No. 14/787,983, dated Feb. 26, 2020.
Final Office Action for copending U.S. Appl. No. 15/324,804, dated Apr. 20, 2020.
Notice of Allowance for copending U.S. Appl. No. 15/541,743, dated Mar. 18, 2020.
Final Office Action for copending U.S. Appl. No. 14/888,002, dated Jun. 1, 2020.
Final Office Action for copending U.S. Appl. No. 15/523,232, dated Oct. 1, 2020.
Non-Final Office Action for copending U.S. Appl. No. 14/787,983, dated Jul. 15, 2020.
Final Office Action for copending U.S. Appl. No. 15/541,741, dated Sep. 17, 2020.
Final Office Action for copending U.S. Appl. No. 14/787,983, dated Feb. 19, 2021.
Non-Final Office Action for copending U.S. Appl. No. 14/888,013, dated May 11, 2021.
International Search Report and Written Opinion for counterpart Application No. PCT/EP2018/055882, dated May 4, 2018.
International Search Report and Written Opinion for counterpart Application No. PCT/EP2018/055889, dated May 4, 2018.
International Search Report and Written Opinion for counterpart Application No. PCT/EP2018/055904, dated Apr. 30, 2018.
Final Office Action for copending U.S. Appl. No. 16/491,375 dated May 26, 2020.
Non-Final Office Action for copending U.S. Appl. No. 16/491,375, dated Nov. 25, 2019.
Non-Final Office Action for copending U.S. Appl. No. 16/491,372, dated May 28, 2020.
NPL search string: IQQueryQuickExport 202005221756, downloaded May 22, 2020.
NPL search string: IQQueryQuickExport 202005221759, downloaded May 22, 2020.
Final Officve Action for copending U.S. Appl. No. 16/491,372, dated Dec. 18, 2020.
Non-Final Office Action for copending U.S. Appl. No. 16/491,374, dated Jan. 14, 2021.
International Search Report for counterpart Application No. PCT/EP2013/059382, dated Jun. 20, 2014.
International Search Report for counterpart Application No. PCT/EP2013/059393, dated Jun. 20, 2014.
Database WPI Week 201172, Thomas Scientific, London, GB, AN 2011-N36295, XP002690571, dated Jan. 25, 2013.
Mintel: Apr. 2010, "Refresh Dry Shampoo," XP002690820.
Mintel: Jun. 2011, "Brown Hair Powder Shampoo," XP002690821.
Oscar Blandi, http://www.skinstore.com/p-6885-oscar-blandi-pronto-dry-shampoo-spray.aspx. Published Jun. 13, 2011.
Non-Final Office Action for copending U.S. Appl. No. 14/399,753, dated Sep. 8, 2015.
Final Office Action for copending U.S. Appl. No. 14/399,753, dated Mar. 30, 2016.
Non-Final Office Action for copending U.S. Appl. No. 14/399,764, dated Dec. 17, 2015.
International Search Report for counterpart Application PCT/EP2014/058896, dated Sep. 23, 2014.
International Search Report and Written Opinion for counterpart Application No. PCT/EP2014/058892, dated Oct. 29, 2014.
International Search Report for counterpart Application No. PCT/EP2014/058894, dated Sep. 29, 2014.
Brunauer, Stephen et al., "Adsorption of Gases in Multimolecular Layers," Journal of the American Chemical Society, vol. 60, Feb. 1938, pp. 309-319.
Final Office Action for copending U.S. Appl. No. 14/399,764, dated Aug. 5, 2016.
Non-Final Office Action for copending U.S. Appl. No. 14/888,002, dated Sep. 9, 2016.
Non-Final Office Action for copending U.S. Appl. No. 14/787,983, dated Sep. 15, 2016.
Final Office Action for copending U.S. Appl. No. 14/399,753, dated Sep. 30, 2016.
Non-Final Office Action for copending U.S. Appl. No. 14/888,013, dated Apr. 13, 2017.
Non-Final Office Action for copending U.S. Appl. No. 14/399,764, dated Mar. 8, 2017.
Final Office Action for copending U.S. Appl. No. 14/787,983, dated May 30, 2017.
International Search Report for counterpart Application PCT/FR2015/051896, dated Oct. 19, 2015.
International Search Report for counterpart Application No. PCT/EP2015/075061, dated Jan. 20, 2016.
International Search Report for PCT/EP2015/075062, dated Jan. 26, 2016.
Mintel: "Code 10 Hair Styling Cream," XP007923186 (Sep. 2001).
Mintel: "One More Day Dry Shampoo," XP007923187 (Aug. 2013).
Mintel: "Foot Deodorant Spray," XP007923193 (Jan. 2014).
Mintel: "72h Anti-Perspirant Deodorant," XP007923192 (Jan. 2014).
Mintel: "Dry Shampoo," XP007923191 (Jan. 2014).
Non-Final Office Action for co-pending U.S. Appl. No. 15/324,804, dated Mar. 5, 2018.
Non-Final Office Action for co-pending U.S. Appl. No. 15/523,232, dated Feb. 23, 2018.

(56) References Cited

OTHER PUBLICATIONS

Bezard et al., "Triglyceride Composition of Coconut Oil," Journal of American Oil Society, 48, 3, Mar. 1971, pp. 134-139.
Non-Final Office Action for co-pending U.S. Appl. No. 15/523,242, dated Aug. 31, 2017.
Final Office Action for co-pending U.S. Appl. No. 14/888,013, dated Aug. 15, 2017.
Final Office Action for co-pending U.S. Appl. No. 14/888,002, dated Sep. 21, 2017.
Final Office Action for copending U.S. Appl. No. 14/399,764, dated Aug. 16, 2017.
Non-Final Office Action for co-pending U.S. Appl. No. 14/399,753, dated Oct. 4, 2017.
Non-Final Office Action for co-pending U.S. Appl. No. 14/787,983, dated May 11, 2018.
Non-Final Office Action for co-pending U.S. Appl. No. 15/523,242, dated Mar. 27, 2018.
International Search Report for counterpart Application No. PCT/EP2011/072617, dated Jul. 5, 2012.
Todd, Charles, et al., "Volatile Silicone Fluids for Cosmetic Formulations," Cosmetics and Toiletries, vol. 91, Jan. 1976, pp. 29-32.
International Search Report for counterpart Application No. PCT/2016/050295, dated Mar. 23, 2016.
International Search Report for counterpart Application No. PCT/EP2016/050299, dated Mar. 23, 2016.
International Search Report for counterpart Application No. PCT/EP2016/050300, dated Mar. 16, 2016.
Non-Final Office Action for co-pending U.S. Appl. No. 15/541,738, dated May 17, 2018.
Non-Final Office Action for co-pending U.S. Appl. No. 13/993,413, dated May 19, 2015.
Final Office Action for co-pending U.S. Appl. No. 13/993,413, dated Dec. 30, 2015.
Non-Final Office Action for co-pending U.S. Appl. No. 13/993,413, dated Nov. 8, 2017.
Final Office Action for co-pending U.S. Appl. No. 13/993,413, dated Jul. 5, 2018.
Oxford Dictionary, Half-Ester, http://www.oxfordreference.com/view/10.1093/acref/9780198529170.001.0001/acref-9780198529170-e-8589, retrieved online on Oct. 19, 2017 (Year: 2017).
Final Office Action for co-pending U.S. Appl. No. 15/324,804, dated Nov. 30, 2018.
International Search Report for PCT/EP2015/064780, dated Sep. 14, 2015.
Porter, M.R., "Handbook of Surfactants," published by Blackie & Son (Glasgow and London), 1991, pp. 116-178.
MINTEL: "Styling Mousse," XP002736036, Nov. 2008.
Non-Final Office Action for copending U.S. Appl. No. 15/541,741, dated May 27, 2021.
Final Office Action for copending U.S. Appl. No. 16/491,374, dated Jun. 28, 2021.
Non-Final Office Action for copending U.S. Appl. No. 16/491,372, dated Jul. 12, 2021.
Final Office Action for copending U.S. Appl. No. 14/888,013, dated Sep. 3, 2021.
Non-Final Office Action for copending U.S. Appl. No. 14/888,002, dated Sep. 3, 2021.

* cited by examiner

AEROSOL DEVICE BASED ON A CALCIUM SALT, ON A FIXING POLYMER, ON A SURFACTANT AND ON WATER

CROSS REFERENCE TO RELATED APPLICATIONS

This is a national stage application of PCT/EP2015/064780, filed internationally on Jun. 30, 2015, which claims priority to French Application No. 1456128, filed on Jun. 30, 2014, both of which are incorporated herein by reference in their entireties.

The present invention relates to an aerosol device comprising a composition based on at least one water-insoluble calcium salt, on at least one fixing polymer and on at least one surfactant in water, and to the use thereof for treating the hair, in particular for shaping the hair and/or retaining the hairstyle.

The hair products for shaping and/or retaining the hairstyle that are the most widespread on the cosmetics market are spray compositions, such as lacquers, sprays and mousses. They essentially consist of an aqueous or aqueous-alcoholic solution and of one or more materials, generally polymeric resins, also referred to as fixing components, the function of which is to form joins between the individual hairs, as a mixture with various cosmetic adjuvants.

These products make it possible to ensure the fixing and the shape retention of the hairstyle over time, but they have a tendency to set rigid the head of hair, giving the impression of having a helmet, referred to as helmet effect. This criterion is often negatively perceived by consumers.

Over the course of the day, if the user runs their hands through the hair, the fixing provided by these hair products is reduced. To date, the polymers conventionally used do not make it possible to re-establish the shape of the hairstyle if it has been disrupted.

The volume of the hairstyle also has a tendency to greatly decrease during the day, particularly for fine hair.

There is therefore a need to provide products which make it possible to fix and retain the hairstyle more naturally, without setting rigid the head of hair, and which make it possible to re-establish the shape of the hairstyle.

The applicant has found, surprisingly and advantageously, that the combination of a water-insoluble calcium salt with a fixing polymer and with a surfactant in water, the whole mixture being packaged in an aerosol device in the presence of less than 20% by weight of propellant, relative to the total weight of the combination and of the propellant, makes it possible to obtain a mousse which gives the hairstyle volume, texturization (i.e. a provision of material, of density, with a feeling of thicker hair), mass (i.e. an impression that there is a greater amount of hair) and shape retention without a set-rigid effect.

One subject of the invention is thus an aerosol device which contains a preferably cosmetic composition comprising:
(i) one or more water-insoluble calcium salts,
(ii) one or more fixing polymers,
(iii) one or more surfactants,
(iv) water, preferably in an amount of greater than 5% by weight relative to the total weight of the composition,
(v) less than 20% by weight, relative to the total weight of the composition, of one or more propellants.

This particular combination allows shaping and/or retention of the hairstyle by texturization without setting it rigid.

It also makes it possible to re-establish the shape of the hairstyle even after it has been intentionally or unintentionally modified. The hairstyle may also be remodeled during the day, without further application of product.

This combination also has a particularly notable effect on the volume of the hairstyle.

A significant decrease in the white effect perceived on the hair with products based on solid particles is also obtained.

The composition according to the invention can be applied both to wet hair and to dry hair.

The present invention also relates to a process for treating, and in particular for shaping the hair and/or retaining the hairstyle, which comprises spraying, onto the hair, the composition according to the invention.

The subject of the present invention is also the use of the composition sprayed from this aerosol device, for shaping the hair and/or retaining the hairstyle, and in particular for giving the hairstyle volume.

Other subjects, characteristics, aspects and advantages of the invention will emerge even more clearly on reading the description and the example that follows.

In the text hereinbelow, and unless otherwise indicated, the limits of a range of values are included within this range, in particular in the expressions "between" and "ranging from . . . to . . . ".

Moreover, the expression "at least one" used in the present description is equivalent to the expression "one or more".

According to the invention, the aerosol device contains a composition comprising:
(i) one or more water-insoluble calcium salts, preferably having a mean particle size ranging from 2 µm to 50 µm,
(ii) one or more fixing polymers,
(iii) one or more surfactants,
(iv) water, preferably in an amount of greater than 5% by weight relative to the total weight of the composition,
(v) less than 20% by weight, relative to the total weight of the composition, of one or more propellants.

For the purposes of the present invention, the term "water-insoluble" is intended to mean a compound of which the solubility at spontaneous pH in water at 25° C. and at atmospheric pressure is less than 0.1% by weight relative to the total weight of the aqueous solution of said compound (i.e. of the solution consisting of said compound and water).

For the purposes of the present invention, the term "spontaneous pH" is intended to mean the pH of the solution comprising the compound and no added pH-adjusting agent.

The calcium salt may be mineral or organic. It is preferably mineral.

As water-insoluble calcium salt, mention may in particular be made of calcium carbonate or calcium stearate. The calcium salt is preferably calcium carbonate.

The water-insoluble calcium salt is in particular in the form of a powder comprising particles which preferably have a mean diameter of from 2 to 50 µm, preferably from 5 to 40 µm, better still about 30 µm.

The calcium salt(s) is (are) present in an amount ranging preferably from 0.1% to 15% by weight, even better still from 0.5% to 10% by weight and even more preferentially from 0.7% to 6% by weight, relative to the total weight of the composition.

As previously indicated, the composition according to the invention comprises one or more fixing polymers.

The term "fixing polymer" is intended to mean any polymer that is capable of giving a shape to a head of hair or of retaining a head of hair in a given shape.

The fixing polymer(s) used in the aerosol device according to the invention are chosen from anionic, cationic, amphoteric and non-ionic fixing polymers, and mixtures thereof.

Anionic fixing polymers that may be mentioned include polymers containing groups derived from carboxylic, sulfonic or phosphoric acids, and having a number-average molecular weight of between 500 and 5 000 000.

The carboxylic groups are provided by unsaturated monocarboxylic or dicarboxylic acid monomers, such as those conforming to the formula:

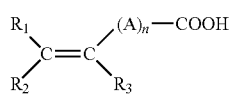
(I)

in which n is an integer from 0 to 10, A denotes a methylene group which is optionally connected to the carbon atom of the unsaturated group or to the neighbouring methylene group when n is greater than 1, via a heteroatom such as oxygen or sulfur, $R_1$ denotes a hydrogen atom or a phenyl or benzyl group, $R_2$ denotes a hydrogen atom, an alkyl group containing from 1 to 4 carbon atoms, or a carboxyl group, $R_3$ denotes a hydrogen atom, an alkyl group containing from 1 to 4 carbon atoms, or a —$CH_2$—COOH, phenyl or benzyl group.

In the formula (I) above, the alkyl group containing from 1 to 4 carbon atoms may in particular denote methyl and ethyl groups.

The anionic fixing polymers containing carboxylic or sulfonic groups that are preferred are:

A) Copolymers of acrylic or methacrylic acid or salts thereof, including copolymers of acrylic acid and acrylamide, and methacrylic acid/acrylic acid/ethyl acrylate/methyl methacrylate copolymers, more particularly Amerhold DR 25 sold by the company Amerchol, and sodium salts of polyhydroxycarboxylic acids. Mention may also be made of methacrylic acid/ethyl acrylate copolymers, in particular in aqueous dispersion, such as Luviflex Soft and Luvimer MAE, which are sold by the company BASF.

B) Copolymers of acrylic or methacrylic acids with a monoethylenic monomer such as ethylene, styrene, vinyl esters, acrylic or methacrylic acid esters, which are optionally grafted on a polyalkylene glycol such as polyethylene glycol, and are optionally crosslinked. Such polymers are described in particular in French patent 1 222 944 and German patent application No. 2 330 956, the copolymers of this type comprising an optionally N-alkylated and/or hydroxyalkylated acrylamide unit in their chain as described especially in Luxembourg patent applications 75370 and 75371. Mention may also be made of copolymers of acrylic acid and $C_1$-$C_4$ alkyl methacrylate.

As another anionic fixing polymer from this class, mention may also be made of the butyl acrylate/acrylic acid/methacrylic acid branched block anionic polymer sold under the name Fixate G-100 L by the company Lubrizol (INCI name AMP-Acrylates/Allyl Methacrylate Copolymer).

C) Copolymers derived from crotonic acid, such as those including in their chain vinyl propionate or acetate units, and optionally other monomers such as allylic or methallylic esters, vinyl ethers or vinyl esters of a linear or branched, saturated carboxylic acid with a long hydrocarbon-based chain, such as those containing at least 5 carbon atoms, it being possible optionally for these polymers to be grafted and crosslinked, or else a vinyl, allylic or methallylic ester of an α- or β-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by the company National Starch.

Mention may also be made, as copolymer derived from crotonic acid, of crotonic acid/vinyl acetate/vinyl tert-butylbenzoate terpolymers, and in particular Mexomere PW supplied by the company Chimex.

D) Polymers derived from maleic, fumaric and/or itaconic acids or anhydrides with vinyl esters, vinyl ethers, vinyl halides, phenylvinyl derivatives, acrylic acid and its esters; these polymers may be esterified. Polymers of these kinds are described in particular in U.S. Pat. Nos. 2,047,398, 2,723,248 and 2,102,113, and in patent GB 839 805, and in particular are those sold under the names Gantrez® AN or ES by the company ISP.

Polymers also falling within this category are the copolymers of maleic, citraconic and/or itaconic anhydrides and of an allylic or methallylic ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the applicant.

E) Polyacrylamides comprising carboxylate groups.

F) Polymers comprising sulfonic groups. These polymers may be polymers comprising vinylsulfonic, styrenesulfonic, naphthalenesulfonic, acrylamidoalkylsulfonic or sulfoisophthalate units.

These polymers can in particular be chosen from:
polyvinylsulfonic acid salts having a molecular weight of between approximately 1000 and 100 000, and also copolymers with an unsaturated comonomer, such as acrylic or methacrylic acids and their esters, and also acrylamide or its derivatives, vinyl ethers and vinylpyrrolidone;
polystyrenesulfonic acid salts, sodium salts, with a molecular weight of about 500 000 and of about 100 000. These compounds are described in patent FR 2198719;
polyacrylamidesulfonic acid salts such as those mentioned in U.S. Pat. No. 4,128,631.

G) Grafted anionic silicone polymers.

The grafted silicone polymers used are preferably chosen from polymers containing a non-silicone organic backbone grafted with monomers containing a polysiloxane, polymers containing a polysiloxane backbone grafted with non-silicone organic monomers, and mixtures thereof.

H) Anionic polyurethanes, possibly comprising silicone grafts and silicones containing hydrocarbon-based grafts.

Examples of fixing polyurethanes may include, in particular, the dimethylolpropionic acid/isophorone diisocyanate/neopentyl glycol/polyesterdiol copolymer (also known under the name polyurethane-1, INCI nomenclature) sold under the brand name Luviset® PUR by the company BASF, and the dimethylolpropionic acid/isophorone diisocyanate/neopentyl glycol/polyesterdiol/silicone diamine copolymer (also known under the name polyurethane-6, INCI nomenclature) sold under the brand name Luviset® Si PUR A by the company BASF.

Another anionic polyurethane that can also be used is Avalure UR 450.

It is also possible to use polymers containing sulfoisophthalate groups, such as the polymers AQ55 and AQ48 sold by the company Eastman.

According to the invention, the anionic fixing polymers are preferably chosen from acrylic acid copolymers, such as the acrylic acid/ethyl acrylate/N-tert-butylacrylamide terpolymer sold under the name Ultrahold Strong® by the company BASF, methacrylic acid/ethyl acrylate copolymers, in particular in aqueous dispersion, such as Luviflex Soft and Luvimer MAE sold by the company BASF, crotonic acid-derived copolymers, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids or anhydrides with vinyl esters, vinyl ethers, vinyl halides, phenylvinyl derivatives, acrylic acid and its esters, such as the monoesterified methyl vinyl ether/maleic anhydride copolymer sold under the name Gantrez® ES 425 by the company ISP, Luviset Si PUR, Mexomere PW, elastomeric or non-elastomeric anionic polyurethanes, polymers comprising sulfoisophthalate groups, and anionic fixing polymers of the B) class; and even more particularly use is preferably made of the butyl acrylate/acrylic acid/methacrylic acid branched block anionic polymer sold under the name Fixate G-100 L by the company Lubrizol (INCI name AMP-Acrylates/Allyl Methacrylate Copolymer).

The cationic fixing polymers that may be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Mention may more particularly be made, among these polymers, of the following cationic polymers:

(1) Homopolymers or copolymers derived from acrylic or methacrylic esters or amides and comprising at least one of the units of following formulae:

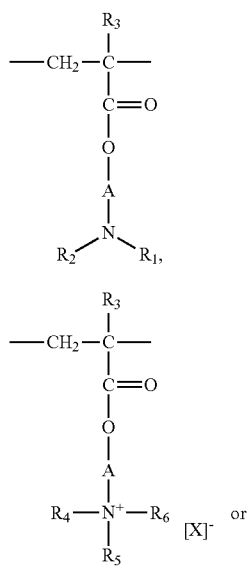

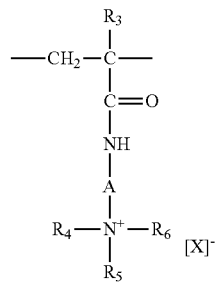

in which:

$R_3$ denotes a hydrogen atom or a $CH_3$ group;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group having from 1 to 18 carbon atoms, or a benzyl group;

$R_1$ and $R_2$, which may be identical or different, each represent a hydrogen atom or an alkyl group having from 1 to 6 carbon atoms;

X denotes a methosulfate anion or a halide, such as chloride or bromide.

The copolymers of class (1) further contain one or more units deriving from comonomers which may be chosen from the class of acrylamides, methacrylamides, diacetone acrylamides, acrylamides and methacrylamides substituted on the nitrogen by $C_1$-$C_4$ alkyl groups, groups derived from acrylic or methacrylic acids or esters thereof, vinyllactams such as vinylpyrrolidone or vinylcaprolactam, and vinyl esters.

Thus, mention may be made, among these copolymers of class (1), of:

copolymers of acrylamide and of dimethylaminoethyl methacrylate which is quaternized with dimethyl sulfate or with a dimethyl halide, such as that sold under the name Hercofloc® by the company Hercules, copolymers of acrylamide and of methacryloyloxyethyltrimethylammonium chloride, described for example in patent application EP-A-080976 and sold under the name Bina Quat P 100 by the company Ciba Geigy, the copolymer of acrylamide and of methacryloyloxyethyltrimethylammonium methosulfate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573, polymers comprising a fatty chain and comprising a vinylpyrrolidone unit, such as the products sold under the names Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the products sold under the name Gafquat® HS 100 by the company ISP.

(2) Cationic guar gums, preferably containing quaternary ammonium, such as those described in U.S. Pat. Nos. 3,589,578 and 4,031,307, such as guar gums containing trialkylammonium cationic groups. Such products are sold in particular under the trade names of Jaguar C13 S, Jaguar C 15 and Jaguar C 17 by Meyhall.

(3) Quaternary copolymers of vinylpyrrolidone and of vinylimidazole.

(4) Chitosans or salts thereof; the salts which can be used are in particular the acetate, lactate, glutamate, gluconate or pyrrolidone carboxylate of chitosan.

These compounds may include the chitosan having a degree of deacetylation of 90.5% by weight which is sold under the name Kytan Brut Standard by the company Aber Technologies, and the chitosan pyrrolidone carboxylate which is sold under the name Kytamer® PC by the company Amerchol.

(5) Cationic cellulose derivatives, such as copolymers of cellulose or of cellulose derivatives grafted with a water-soluble monomer comprising a quaternary ammonium and described in particular in the U.S. Pat. No. 4,131,576, such as hydroxyalkylcelluloses, for example hydroxymethyl-, hydroxyethyl- or hydroxypropylcelluloses, grafted in particular with a methacryloyloxyethyltrimethylammonium, methacrylamidopropyltrimethyl-ammonium or dimethyl-diallylammonium salt.

The commercial products corresponding to this definition are more particularly the products sold under the name Celquat L 200 and Celquat H 100 by the company National Starch, or else Celquat LOR by the company Akzo Nobel, and correspond to polyquaternium-4.

(6) Polymers comprising in their structure:
(a) one or more units corresponding to formula (A1) below:

(b) optionally one or more units corresponding to formula (B1) below:

In other words, these polymers may be chosen in particular from homopolymers or copolymers comprising one or more units derived from vinylamine and optionally one or more units derived from vinylformamide. Mention may, for example, be made of vinylamine/vinylformamide copolymers such as the product provided by the company BASF under the trade name Luviquat 9030, having the INCI name vinylamine/vinylformamide copolymer.

The preferred cationic fixing polymers are in particular chosen from those of class (5) or of class (6). More particularly, the cationic fixing polymer may be chosen from the hydroxyethylcellulose/diallyldimethylammonium chloride copolymer having the INCI name polyquaternium-4, and the vinylamine/vinylformamide copolymer having the INCI name vinylamine/vinylformamide copolymer.

The amphoteric fixing polymers that can be used in accordance with the invention can be chosen from polymers comprising units B and C distributed randomly in the polymer chain, in which B denotes a unit deriving from a monomer comprising at least one basic nitrogen atom and C denotes a unit deriving from an acid monomer comprising one or more carboxylic or sulfonic groups, or alternatively B and C can denote groups deriving from carboxybetaine or sulfobetaine zwitterionic monomers; B and C can also denote a cationic polymer chain comprising primary, secondary, tertiary or quaternary amine groups, in which at least one of the amine groups bears a carboxylic or sulfonic group connected via a hydrocarbon-based group, or alternatively B and C form part of a chain of a polymer containing an ethylenedicarboxylic unit in which one of the carboxylic groups has been made to react with a polyamine comprising one or more primary or secondary amine groups.

The amphoteric fixing polymers corresponding to the definition given above that are more particularly preferred are chosen from the following polymers:

1) Polymers resulting from the copolymerization of a monomer derived from a vinyl compound bearing a carboxylic group, such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylamino-alkylmethacrylamide and -acrylamide. Such compounds are described in the U.S. Pat. No. 3,836,537.

The vinyl compound may also be a dialkyldiallylammonium salt such as diethyldiallylammonium chloride.

2) Polymers containing units deriving:

a) from at least one monomer chosen from acrylamides or methacrylamides which are substituted on the nitrogen by an alkyl group, b) from at least one acidic comonomer comprising one or more reactive carboxylic groups, and c) from at least one basic comonomer, such as esters with primary, secondary, tertiary and quaternary amine substituents of acrylic and methacrylic acids, and the product of quaternization of dimethylaminoethyl methacrylate with dimethyl or diethyl sulfate.

The N-substituted acrylamides or methacrylamides which are more particularly preferred according to the invention are groups in which the alkyl groups contain from 2 to 12 carbon atoms, and more particularly N-ethylacrylamide, N-tert-butylacrylamide, N-tert-octylacrylamide, N-octylacrylamide, N-decylacrylamide, N-dodecylacrylamide, and also the corresponding methacrylamides.

The acidic comonomers are chosen more particularly from acrylic, methacrylic, crotonic, itaconic, maleic and fumaric acids and also the alkyl monoesters having 1 to 4 carbon atoms of maleic or fumaric acids or anhydrides. The preferred basic comonomers are aminoethyl, butylaminoethyl, N,N'-dimethylaminoethyl and N-tert-butylaminoethyl methacrylates. The copolymers of which the CTFA (4th edition, 1991) name is octylacrylamide/acrylates/butylaminoethyl methacrylate copolymer, such as the products sold under the name Amphomer® or Lovocryl® 47 by the company National Starch, are particularly used.

3) Alkylated and crosslinked polyaminoamides deriving wholly or partly from polyaminoamides of general formula:

in which $R_4$ represents a divalent group derived from a saturated dicarboxylic acid, from a mono- or dicarboxylic aliphatic acid with an ethylenic double bond, from an ester of an alcohol containing 1 to 6 carbon atoms with these acids, or from a group deriving from the addition of any one of said acids with a bis-primary amine or bis-secondary-derived amine, and Z denotes a group of a bis-primary or mono- or bis-secondary polyalkylene-polyamine, and preferably represents:

a) in proportions of from 60 mol % to 100 mol %, the group

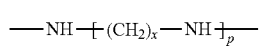 (III)

where x=2 and p=2 or 3, or else x=3 and p=2, this group deriving from diethylenetriamine, triethylenetetramine or dipropylenetriamine;

b) in proportions of from 0 to 40 mol %, the group (III) above, in which x=2 and p=1, which derives from ethylenediamine, or the group deriving from piperazine

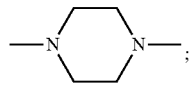

c) in proportions of from 0 to 20 mol %, the group —NH—(CH$_2$)$_6$—NH— deriving from hexamethylenediamine, these polyaminoamines being crosslinked by addition of a difunctional crosslinking agent chosen from epihalohydrins, diepoxides, dianhydrides, bis-unsaturated derivatives, by means of 0.025 to 0.35 mol of crosslinking agent per amine group of the polyaminoamide, and being alkylated by the action of acrylic acid, chloroacetic acid or an alkane sultone or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, and acids having an ethylenic double bond, such as, for example, acrylic, methacrylic and itaconic acids. The alkane sultones used in the alkylation are preferably propane sultone or butane sultone; the salts of the alkylating agents are preferably the sodium or potassium salts.

4) Polymers containing zwitterionic units of formula:

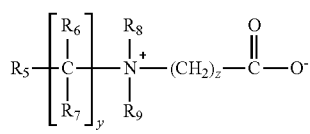 (IV)

in which R$_5$ denotes a polymerizable unsaturated group, such as an acrylate, methacrylate, acrylamide or methacrylamide group, y and z each represent an integer from 1 to 3, R$_6$ and R$_7$ represent a hydrogen atom or a methyl, ethyl or propyl group, R$_8$ and R$_9$ represent a hydrogen atom or an alkyl group such that the sum of the carbon atoms in R$_{10}$ and R$_{11}$ does not exceed 10.

The polymers comprising such units can also comprise units derived from non-zwitterionic monomers such as dimethyl- or diethylaminoethyl acrylate or methacrylate or alkyl acrylates or methacrylates, acrylamides or methacrylamides or vinyl acetate.

5) Polymers derived from chitosan, containing monomer units conforming to the following formulae:

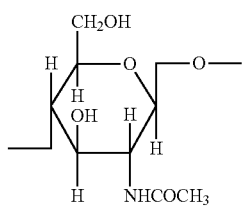 (V)

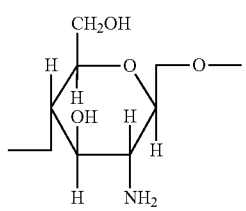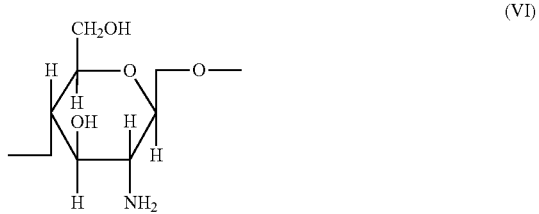 (VI)

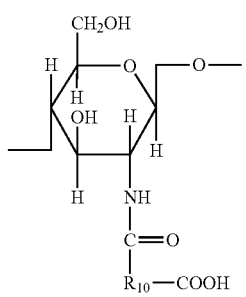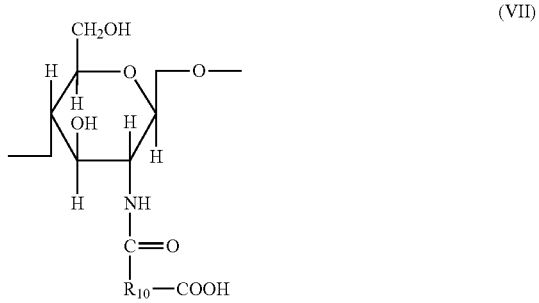 (VII)

the unit (V) being present in proportions of between 0 and 30%, the unit (VI) in proportions of between 5% and 50% and the unit (VII) in proportions of between 30% and 90%, it being understood that, in this unit F, R$_{10}$ represents a group of formula:

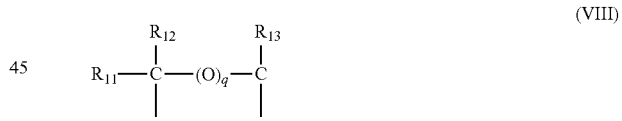 (VIII)

in which, if q=0, R$_{11}$, R$_{12}$ and R$_{13}$, which may be identical or different, each represent a hydrogen atom, a methyl, hydroxyl, acetoxy or amino residue, a monoalkylamine residue or a dialkylamine residue that are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the groups R$_{17}$, R$_{18}$ and R$_{19}$ being, in this case, a hydrogen atom;

or, if q=1, R$_{11}$, R$_{12}$ and R$_{13}$ each represent a hydrogen atom, as well as the salts formed by these compounds with bases or acids.

6) Polymers derived from the N-carboxyalkylation of chitosan.

7) Polymers of units corresponding to the general formula (IX) described, for example, in French patent 1 400 366:

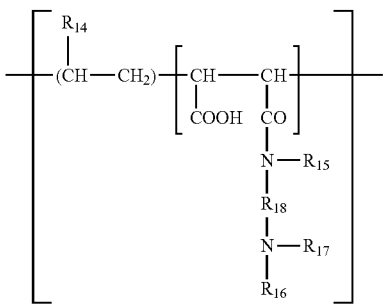

(IX)

in which $R_{14}$ represents a hydrogen atom or a $CH_3O$, $CH_3CH_2O$, or phenyl group, $R_{15}$ denotes hydrogen or a $C_1$-$C_4$ alkyl group such as methyl and ethyl, $R_{16}$ denotes hydrogen or a $C_1$-$C_4$ alkyl group such as methyl and ethyl, $R_{17}$ denotes a $C_1$-$C_4$ alkyl group such as methyl and ethyl or a group conforming to the formula: —$R_{18}$—$N(R_{16})_2$, with $R_{18}$ representing a —$CH_2$—$CH_2$—, —$CH_2$—$CH_2$—$CH_2$—, or —$CH_2$—$CH(CH_3)$— group and $R_{16}$ having the meanings given above, and also the higher homologues of these groups, containing up to 6 carbon atoms.

8) Amphoteric polymers of the type -D-X-D-X—, chosen from:

a) polymers obtained by the action of chloroacetic acid or sodium chloroacetate on compounds comprising at least one unit of formula:

-D-X-D-X-D-     (X)

where D denotes a group

and X denotes the symbol E or E', where E or E', which may be identical or different, denote a divalent group which is an alkylene group having a straight or branched chain that contains up to 7 carbon atoms in the main chain and is unsubstituted or substituted by hydroxyl groups, and may further comprise oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) polymers of formula:

-D-X-D-X—     (XI)

where D denotes a group

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate.

9) ($C_1$-$C_5$)Alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

According to a preferred embodiment of the invention, the amphoteric fixing polymers that may be used in the aerosol device according to the invention may be chosen from branched block copolymers comprising:

(a) non-ionic units derived from at least one monomer chosen from $C_1$-$C_{20}$ alkyl (meth)acrylates, N-mono-($C_2$-$C_{12}$ alkyl)-(meth)acrylamides and N,N-di($C_2$-$C_{12}$ alkyl)(meth)acrylamides, (b) anionic units derived from at least one monomer chosen from acrylic acid and methacrylic acid, and (c) polyfunctional units derived from at least one monomer containing at least two polymerizable unsaturated functional groups, and preferably having a structure consisting of hydrophobic blocks onto which are fixed, via polyfunctional units (c), several more hydrophilic blocks.

Preferably, the amphoteric polymers have at least two glass transition temperatures (Tg), at least one of which is greater than 20° C. and the other is less than 20° C.

The preferred amphoteric polymers are polymers comprising units deriving:

a) from at least one monomer chosen from acrylamides or methacrylamides substituted on the nitrogen with an alkyl group, b) from at least one acidic comonomer comprising one or more reactive carboxylic groups, and c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

Mention may be made in particular of the polymers sold under the name Amphomer by the company National Starch.

The non-ionic fixing polymers which can be used according to the present invention are chosen, for example, from:
polyalkyloxazolines,
vinyl acetate homopolymers,
vinyl acetate copolymers, for instance copolymers of vinyl acetate and acrylic ester, copolymers of vinyl acetate and ethylene, or copolymers of vinyl acetate and maleic ester, for example dibutyl maleate,
acrylic ester homopolymers and copolymers, for instance copolymers of alkyl acrylates and of alkyl methacrylates, such as the products provided by the company Rohm & Haas under the names Primal® AC-261 K and Eudragit® NE 30 D, by the company BASF under the name 8845, or by the company Hoechst under the name Appretan® N9212,
copolymers of acrylonitrile and a non-ionic monomer chosen, for example, from butadiene and alkyl (meth)acrylates, such as the products provided under the name CJ 0601 B by the company Rohm & Haas, styrene homopolymers, styrene copolymers, for instance copolymers of styrene and of alkyl (meth)acrylate, such as the products Mowilith® LDM 6911, Mowilith® DM 611 and Mowilith® LDM 6070 provided by the company Hoechst, the products Rhodopas® SD 215 and Rhodopas® DS 910 provided by the company Rhône-Poulenc, copolymers of styrene, alkyl methacrylate and alkyl acrylate, copolymers of styrene and butadiene, or copolymers of styrene, butadiene and vinylpyridine, polyamides, vinyllactam homopolymers such as vinylpyrrolidone homopolymers and such as the polyvinylcaprolactam sold under the name Luviskol® Plus by the company BASF, vinyllactam copolymers such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF and poly(vinylpyrrolidone/vinyl acetate/vinyl propionate) terpolymers, for instance the product sold under the name Luviskol® VAP 343 by the company BASF, and poly(vinyl alcohols).

The alkyl groups of the non-ionic polymers mentioned above preferably have from 1 to 6 carbon atoms.

Preferably, the fixing polymer(s) used in the aerosol device according to the invention is (are) anionic, non-ionic or cationic fixing polymers, in particular fixing polymers chosen from acrylic acid copolymers, such as the acrylic acid/ethyl acrylate/N-tert-butylacrylamide terpolymer, methacrylic acid/ethyl acrylate copolymers, in particular in aqueous dispersion, crotonic acid-derived copolymers, such as the vinyl acetate/vinyl tert-butylbenzoate/crotonic acid terpolymers and the crotonic acid/vinyl acetate/vinyl neododecanoate terpolymers, polymers derived from maleic, fumaric or itaconic acids or anhydrides with vinyl esters, vinyl ethers, vinyl halides, phenylvinyl derivatives, acrylic acid and its esters, such as the monoesterified methyl vinyl ether/maleic anhydride copolymer, elastomeric or non-elastomeric anionic polyurethanes, polymers comprising sulfoisophthalate groups, the butyl acrylate/acrylic acid/methacrylic acid branched block anionic polymer; vinyllactam homopolymers, such as vinylpyrrolidone homopolymers and polyvinylcaprolactam, vinyllactam copolymers, such as a poly(vinylpyrrolidone/vinyllactam) copolymer and poly(vinylpyrrolidone/vinyl acetate) copolymers; cationic cellulose derivatives, such as copolymers of cellulose or of cellulose derivatives grafted with a water-soluble monomer comprising a quaternary ammonium, and more particularly hydroxyalkylcelluloses, for instance hydroxymethyl-, hydroxyethyl- or hydroxypropylcelluloses grafted in particular with a methacryloyloxyethyltrimethylammonium, methacrylamidopropyl-trimethylammonium, or dimethyldiallylammonium salt, and vinylamine/vinylformamide copolymers.

More preferentially, the fixing polymer(s) used in the aerosol device according to the invention is (are) chosen from the butyl acrylate/acrylic acid/methacrylic acid branched block anionic polymer, vinyllactam homopolymers and copolymers, such as polyvinylcaprolactam and the vinylpyrrolidone/vinyl acetate polymer, the vinylamine/vinylformamide copolymer, polyquaternium-4, and mixtures thereof.

The fixing polymer(s) is (are) present in an amount ranging preferably from 0.1% to 15% by weight, even better still from 0.5% to 10% by weight and even more preferentially from 1% to 8% by weight, relative to the total weight of the composition.

The surfactants that can be used in the composition according to the invention may be anionic, non-ionic, amphoteric or zwitterionic or cationic.

The term "anionic surfactant" is intended to mean a surfactant comprising, as ionic or ionizable groups, only anionic groups. These anionic groups are preferably chosen from the following groups: $-CO_2H$, $-CO_2^-$, $-SO_3H$, $-SO_3^-$, $-OSO_3H$, $-OSO_3^-$, $-H_2PO_3$, $-HPO_3^-$, $-PO_3^{2-}$, $-H_2PO_2$, $-HPO_2^-$, $-PO_2^{2-}$, $-POH$ or $-PO^-$.

Mention may be made, as examples of anionic surfactants which can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and preferably from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactants are in the form of salts, it (they) can be chosen from alkali metal salts, such as the sodium or potassium salt and preferably the sodium salt, the ammonium salts, the amine salts and in particular the aminoalcohol salts, or the alkaline-earth metal salts, such as the magnesium salt.

Mention may in particular be made, as examples of aminoalcohol salts, of mono-, di- or triethanolamine salts, mono-, di- or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts and in particular sodium or magnesium salts.

In a first variant, the anionic surfactants can be chosen from $(C_6$-$C_{24})$alkyl sulfates, $(C_6$-$C_{24})$alkyl ether sulfates comprising from 2 to 50 ethylene oxide units, in particular in the form of alkali metal, ammonium, aminoalcohol and alkaline-earth metal salts, or a mixture of these compounds.

Even better still, it is preferred to use in this variant $(C_{12}$-$C_{20})$alkyl sulfates, $(C_{12}$-$C_{20})$alkyl ether sulfates comprising from 2 to 20 ethylene oxide units, in particular in the form of alkali metal, ammonium, aminoalcohol and alkaline-earth metal salts, or a mixture of these compounds. Even better still, sodium lauryl ether sulfate containing 2.2 mol of ethylene oxide is preferred.

In a second variant, the anionic surfactants can be chosen from surfactants comprising anionic groups chosen from $-C(O)OH$, $-C(O)O^-$, $-SO_3H$ or $-S(O)_2O^-$, such as alkylsulfonates, alkylamide sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates, N-acyltaurates, acyl lactylates or N-acylglycinates, the alkyl and acyl groups of all these compounds comprising from 6 to 40 carbon atoms and preferably from 6 to 24 carbon atoms.

Most particularly, use may be made of ($C_6$-$C_{40}$ acyl)glutamates, better still ($C_6$-$C_{24}$ acyl)glutamates, for instance the disodium cocoyl glutamate provided under the trade name Plantapon ACG LC by the company BASF, or ($C_6$-$C_{40}$ acyl)isethionates and better still ($C_6$-$C_{24}$ acyl)isethionates, for instance the sodium lauroyl methyl isethionate sold by the company Innospec under the trade name Iselux LQ-CLR-SB.

Examples of non-ionic surfactants that may be used in the composition according to the invention are described, for example, in the Handbook of Surfactants by M. R. Porter, published by Blackie & Son (Glasgow and London), 1991, pp. 116-178. They are in particular chosen from polyethoxylated, polypropoxylated and/or polyglycerolated alcohols, α-diols and ($C_1$-$C_{20}$)alkylphenols, containing at least one fatty chain comprising, for example, from 8 to 18 carbon atoms, the number of ethylene oxide and/or propylene oxide groups possibly ranging in particular from 2 to 50, and the number of glycerol groups possibly ranging in particular from 2 to 30.

Mention may also be made of condensates of ethylene oxide and of propylene oxide with fatty alcohols, polyethoxylated fatty amides preferably having from 2 to 30 ethylene oxide units, polyglycerolated fatty amides comprising on average from 1 to 5 glycerol groups, and in particular from 1.5 to 4, ethoxylated fatty acid esters of sorbitan containing from 2 to 30 ethylene oxide units, fatty acid esters of sucrose, fatty acid esters of polyethylene glycol, ($C_6$-$C_{24}$ alkyl)mono- or polyglycosides, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides, or else vegetable oils, which are optionally hydrogenated, and in particular polyethoxylated vegetable oils preferably having from 2 to 60 ethylene oxide units, better still from 10 to 50 ethylene oxide units.

The non-ionic surfactants which are particularly preferred are chosen from polyethoxylated alcohols, the alcohols comprising in particular from 8 to 18 carbon atoms and the number of ethylene oxide groups ranging in particular from 2 to 50, and vegetable oils, which are optionally hydrogenated, and in particular polyethoxylated vegetable oils preferably having from 2 to 60 ethylene oxide units, better still from 10 to 50 ethylene oxide units.

The amphoteric or zwitterionic surfactants capable of being used in the present invention can in particular be derivatives of optionally quaternized secondary or tertiary aliphatic amines containing at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of ($C_8$-$C_{20}$)alkylbetaines, sulfobetaines, ($C_8$-$C_{20}$)alkylamido($C_1$-$C_6$)alkylbetaines such as cocamidopropylbetaine, and ($C_8$-$C_{20}$)alkylamido($C_1$-$C_6$)alkylsulfobetaines.

Among the optionally quaternized secondary or tertiary aliphatic amine derivatives that may be used, mention may also be made of the products having the following respective structures (XII) and (XIII):

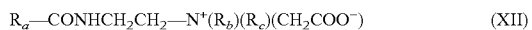

$R_a$—CONHCH$_2$CH$_2$—N$^+$($R_b$)($R_c$)(CH$_2$COO$^-$) (XII)

in which:
$R_a$ represents a $C_{10}$-$C_{30}$ alkyl or alkenyl group derived from an acid $R_a$—COOH preferably present in hydrolysed coconut oil, or a heptyl, nonyl or undecyl group,
$R_b$ represents a β-hydroxyethyl group, and
$R_c$ represents a carboxymethyl group;

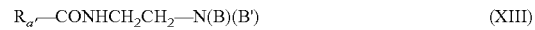

$R_a$—CONHCH$_2$CH$_2$—N(B)(B') (XIII)

in which:
B represents —CH$_2$CH$_2$OX',
X' represents the group —CH$_2$—COOH, CH$_2$—COOZ', —CH$_2$CH$_2$—COOH or —CH$_2$CH$_2$—COOZ', or a hydrogen atom,
B' represents —(CH$_2$)$_z$—Y', with z=1 or 2,
Y' represents —COOH, —COOZ', or the group —CH$_2$—CHOH—SO$_3$H or —CH$_2$—CHOH—SO$_3$Z',
Z' represents an ion derived from an alkali or alkaline-earth metal, such as sodium, potassium or magnesium; an ammonium ion; or an ion derived from an organic amine and in particular from an aminoalcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane,
$R_{a'}$ represents a $C_{10}$-$C_{30}$ alkyl or alkenyl group of an acid $R_{a'}$—COOH preferably present in coconut oil or in hydrolysed linseed oil, an alkyl group, in particular of $C_{17}$ and its iso form, or an unsaturated $C_{17}$ group.

These compounds are also classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (XIIIa):

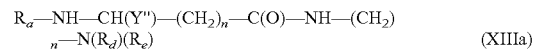

$R_a$—NH—CH(Y'')—(CH$_2$)$_n$—C(O)—NH—(CH$_2$)$_{n'}$—N(R$_d$)(R$_e$)  (XIIIa)

in which formula:
Y'' represents the group —C(O)OH, —C(O)OZ'', —CH$_2$—CH(OH)—SO$_3$H or the group —CH$_2$—CH(OH)—SO$_3$—Z'';
$R_d$ and $R_e$ represent, independently of each other, a $C_1$-$C_4$ alkyl or hydroxyalkyl group;
Z'' represents a cationic counterion derived from an alkali metal or alkaline-earth metal, such as sodium, an ammonium ion or an ion derived from an organic amine;
$R_{a''}$ represents a $C_{10}$-$C_{30}$ alkyl or alkenyl group of an acid $R_{a''}$—C(O)OH preferably present in coconut oil or in hydrolysed linseed oil;
n and n' denote, independently of each other, an integer ranging from 1 to 3.

Among the compounds of formula (XIIIa), mention may be made of the compound classified in the CTFA dictionary under the name sodium diethylaminopropyl cocoaspartamide and sold by the company Chimex under the name Chimexane HB.

Preferably, the amphoteric or zwitterionic surfactants are chosen from ($C_8$-$C_{20}$)alkylbetaines, ($C_8$-$C_{20}$)alkylamido($C_1$-$C_6$)alkylbetaines and ($C_8$-$C_{20}$)alkyl amphodiacetates, and mixtures thereof.

Preferentially, the amphoteric or zwitterionic surfactants are chosen, alone or as a mixture, from cocoylamidopropyl betaine, cocoyl betaine and cocoamphodiacetate.

The cationic surfactant(s) which can be used in the composition according to the invention comprise in particular salts of optionally polyoxyalkylenated primary, secondary or tertiary fatty amines, quaternary ammonium salts, and mixtures thereof.

Mention may in particular be made, as quaternary ammonium salts, for example, of:

those corresponding to the general formula (XIV) below:

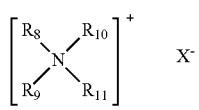

(XIV)

in which the groups $R_8$ to $R_{11}$, which can be identical or different, represent a linear or branched aliphatic group comprising from 1 to 30 carbon atoms or an aromatic group, such as aryl or alkylaryl, at least one of the groups $R_8$ to $R_{11}$ comprising from 8 to 30 carbon atoms and preferably from 12 to 24 carbon atoms. The aliphatic groups can comprise heteroatoms, such as, in particular, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Preference is given, among the quaternary ammonium salts of formula (XIV), on the one hand, to tetraalkylammonium chlorides, such as, for example, dialkyldimethylammonium or alkyltrimethylammonium chlorides, in which the alkyl group comprises approximately from 12 to 22 carbon atoms, in particular behenyltrimethylammonium, distearyldimethylammonium, cetyltrimethylammonium or benzyldimethylstearylammonium chlorides, or also palmitylamidopropyl-trimethylammonium chloride or stearamidopropyldimethyl(myristyl acetate)-ammonium chloride, sold under the name Ceraphyl® 70 by the company Van Dyk;

quaternary ammonium salts of imidazoline, for instance those of formula (XV) below:

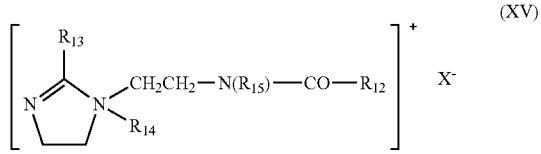

(XV)

in which $R_{12}$ represents an alkenyl or alkyl group comprising from 8 to 30 carbon atoms, for example derived from tallow fatty acids, $R_{13}$ represents a hydrogen atom, a $C_1$-$C_4$ alkyl group or an alkenyl or alkyl group comprising from 8 to 30 carbon atoms, $R_{14}$ represents a $C_1$-$C_4$ alkyl group, $R_{15}$ represents a hydrogen atom, a $C_1$-$C_4$ alkyl group, $X^-$ is an anion chosen from the group of halides, phosphates, acetates, lactates, ($C_1$-$C_4$)alkyl sulfates and ($C_1$-$C_4$)alkyl- or ($C_1$-$C_4$)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, particularly of formula (XVI) below:

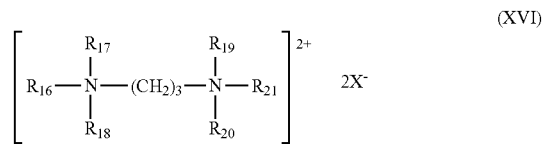

(XVI)

in which $R_{16}$ denotes an alkyl group comprising approximately from 16 to 30 carbon atoms, which is optionally hydroxylated and/or interrupted with one or more oxygen atoms, $R_{17}$ is chosen from hydrogen, an alkyl group comprising from 1 to 4 carbon atoms or a group —$(CH_2)_3$—$N^+(R_{16a})$ $(R_{17a})(R_{18a})$, $R_{16a}$, $R_{17a}$, $R_{18a}$, $R_{18}$, $R_{19}$, $R_{20}$ and $R_{21}$, which may be identical or different, are chosen from hydrogen or an alkyl group comprising from 1 to 4 carbon atoms, and $X^-$ is an anion chosen from the group of halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, provided by the company Finetex (Quatemium 89), and Finquat CT, provided by the company Finetex (Quatemium 75);

quaternary ammonium salts comprising one or more ester functions, such as those of formula (XVII) below:

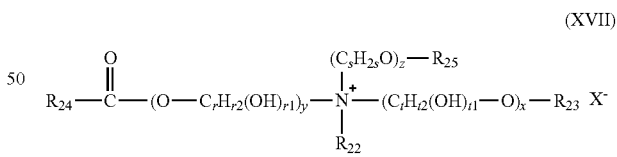

(XVII)

in which:

$R_{22}$ is chosen from $C_1$-$C_6$ alkyl groups and $C_1$-$C_6$ hydroxyalkyl or dihydroxyalkyl groups, $R_{23}$ is chosen from:

the group

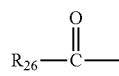

saturated or unsaturated and linear or branched $C_1$-$C_{22}$ hydrocarbon-based groups $R_{27}$,
a hydrogen atom,
$R_{25}$ is chosen from:
the group

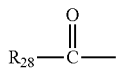

saturated or unsaturated and linear or branched $C_1$-$C_6$ hydrocarbon-based groups $R_{29}$,
a hydrogen atom,
$R_{24}$, $R_{26}$ and $R_{28}$, which may be identical or different, are chosen from linear or branched, saturated or unsaturated $C_7$-$C_{21}$ hydrocarbon-based groups,
r, s and t, which are identical or different, are integers having values from 2 to 6,
r1 and t1, which are identical or different, have the values 0 or 1, r2+r1=2r and t1+t2=2 t,
y is an integer ranging from 1 to 10,
x and z, which may be identical or different, are integers ranging from 0 to 10,
$X^-$ is a simple or complex, organic or mineral anion,
with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group and more particularly a methyl or ethyl group.

Advantageously, the sum x+y+z is from 1 to 10.

When $R_{23}$ is a hydrocarbon-based group $R_{27}$, it can be long and have from 12 to 22 carbon atoms or be short and have from 1 to 3 carbon atoms.

When $R_{25}$ is an hydrocarbon-based group $R_{29}$, it preferably has from 1 to 3 carbon atoms.

Advantageously, $R_{24}$, $R_{26}$ and $R_{28}$, which are identical or different, are chosen from saturated or unsaturated and linear or branched $C_{11}$-$C_{21}$ hydrocarbon-based groups and more particularly from saturated or unsaturated and linear or branched $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate, or a ($C_1$-$C_4$)alkyl- or ($C_1$-$C_4$)alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anion $X^-$ is more particularly still chloride, methyl sulfate or ethyl sulfate.

Use is made more particularly, in the composition according to the invention, of the ammonium salts of formula (XVII) in which:
$R_{22}$ denotes a methyl or ethyl group,
x and y are equal to 1,
z is equal to 0 or 1,
r, s and t are equal to 2,
$R_{23}$ is chosen from:
the group

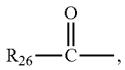

methyl, ethyl or $C_{14}$-$C_{22}$ hydrocarbon-based groups, and
a hydrogen atom
$R_{25}$ is chosen from:
the group

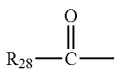

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XVII), examples that may be mentioned include salts, in particular the chloride or methyl sulfate, of diacyloxyethyldimethylammonium, diacyloxyethylhydroxyethylmethylammonium, monoacyloxyethyldihydroxyethylmethylammonium, triacyloxyethylmethyl-ammonium or monoacyloxyethylhydroxyethyldimethylammonium, and mixtures thereof. The acyl groups preferably contain 14 to 18 carbon atoms and are obtained more particularly from a vegetable oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention can comprise, for example, a mixture of quaternary ammonium mono-, di- and triester salts with a predominance by weight of diester salts.

Mention may be made, as examples of such compounds, of distearoylethylhydroxyethylmethylammonium or dipalmitoylethylhydroxyethyl-methylammonium salts, and in particular the methosulfates.

Use may also be made of the ammonium salts containing at least one ester function that are described in U.S. Pat. Nos 4,874,554 and 4,137,180.

Use may also be made of behenoylhydroxypropyltrimethylammonium chloride, for example, sold by the company KAO under the name Quartamin BTC 131.

Preferably, the ammonium salts containing at least one ester function comprise two ester functions.

It is more particularly preferable to choose, among cationic surfactants, cetyltrimethylammonium, behenyltrimethylammonium or dipalmitoylethyl-hydroxyethylmethylammonium salts, and mixtures thereof, and more particularly behenyltrimethylammonium chloride, cetyltrimethylammonium chloride or dipalmitoylethylhydroxyethylammonium methosulfate, and mixtures thereof.

In one particular embodiment of the invention, the hair composition comprises one or more surfactants chosen from ($C_6$-$C_{24}$)alkyl sulfates, ($C_6$-$C_{24}$)alkyl ether sulfates comprising from 2 to 50 ethylene oxide units, in particular in the form of alkali metal salts, ammonium salts, aminoalcohol salts and alkaline-earth metal salts; polyethoxylated $C_8$-$C_{18}$ alcohols, the number of ethylene oxide groups ranging in particular from 2 to 50, vegetable oils, which are optionally hydrogenated, and in particular polyethoxylated vegetable oils preferably having from 2 to 60 ethylene oxide units, better still from 10 to 50 ethylene oxide units; ($C_8$-$C_{20}$) alkylbetaines, ($C_8$-$C_{20}$)alkylamido($C_1$-$C_6$)alkylbetaines and ($C_8$-$C_{20}$)alkyl amphodiacetates; and quaternary ammonium salts of formula (XIV), in particular cetyltrimethylammonium salts; and mixtures thereof.

Preferably, the composition according to the invention contains one or more non-ionic surfactant(s).

The composition according to the invention preferably exhibits a total content of surfactant(s) of less than or equal to 10% by weight, better still of less than 8% by weight and even better still of less than 7.5% by weight, relative to the total weight of the composition.

More particularly, said total content of surfactant(s) can range from 0.05% to 10% by weight, better still from 0.1% to 8% by weight and more preferably still from 0.2% to 5% by weight, relative to the total weight of the composition.

The weight ratio of the total amount of fixing polymer(s) to the total amount of surfactant(s) is preferably greater than or equal to 0.5, better still ranges from 0.5 to 15 and even better still ranges from 0.6 to 8.

The composition according to the invention also contains water.

It preferably contains more than 5% by weight of water, even more preferentially from 20% to 95% by weight and even better still from 50% to 90% by weight of water relative to the total weight of the composition.

Examples of propellants that may be used in the aerosol device of the present invention are liquefied gases such as dimethyl ether, 1,1-difluoroethane, or $C_3$-$C_5$ alkanes, for instance propane, isopropane, n-butane, isobutane or pentane, or compressed gases such as air, nitrogen or carbon dioxide, and mixtures thereof.

Mention may be made preferentially of dimethyl ether, 1,1-difluoroethane and $C_3$-$C_5$ alkanes, for instance propane, n-butane, isobutane and mixtures thereof.

The propellant(s) is (are) present in an amount of less than 20% by weight, preferably less than 15% by weight, even better still ranging from 1% to 14% by weight and even more preferentially from 3% to 12% by weight relative to the total weight of the composition.

In one embodiment, the composition according to the invention also comprises one or more thickening polymers.

By way of examples of thickening polymers, mention may in particular be made of acrylic polymers, polysaccharides and associative polymers.

Preferably, the thickening polymer is chosen from polysaccharides, in particular from cellulose-based polymers or scleroglucan gums.

When it (they) is (are) present, the amount of the thickening polymer(s) preferably ranges from 0.05% to 10% by weight, even better still from 0.05% to 5% by weight and even more preferentially from 0.08% to 2% by weight relative to the total weight of the composition.

The composition contained in the aerosol device according to the invention may also contain one or more additives chosen from silicone derivatives in soluble, dispersed or micro-dispersed forms, solvents such as ethanol, clays such as bentone and hectorite, silica, plasticizers, anti-agglomerating agents, protective screening agents, acids, bases, nacres, flakes and fragrances, permanent or temporary dyes, and treating active agents.

These additives may be present in the composition according to the invention in an amount ranging from 0 to 20% by weight, relative to the total weight of the composition.

Those skilled in the art will take care to choose these optional additives and their amounts so that they do not harm the properties of the compositions of the present invention.

The compositions in accordance with the invention are packaged in an aerosol device that is common in cosmetics.

The aerosol device used for packaging the composition of the invention may consist of an outer aerosol can which contains both the propellant(s) and the other ingredients of the composition in a single compartment. Preferably, said device is equipped with a valve and also comprises a push-button which is equipped with a diffuser.

According to another variant, the aerosol device can be made of two compartments, composed of an outer aerosol can comprising an inner bag hermetically welded to a valve. The various ingredients of the composition are introduced into the inner bag and a compressed gas is introduced between the bag and the can at a sufficient pressure to make the product come out. According to this variant, the device is also equipped with a valve and comprises a push-button which is equipped with a diffuser.

The sprayed compositions are preferably in the form of a mousse.

The present invention also relates to a process for treating, and in particular for shaping the hair and/or retaining the hairstyle, which comprises the use of a composition as described above.

In particular, the process for shaping and/or retaining the hairstyle comprises a step of applying, to dry or wet hair, a composition as previously defined, sprayed from an aerosol device according to the invention, optionally to be rinsed off after an optional leave-on time or after optional drying.

In other words, said process comprises spraying the composition as previously defined from an aerosol device according to the invention, and applying the sprayed composition onto hair.

Preferably, the composition according to the invention is not rinsed off.

The composition according to the invention may thus be used on wet or dry hair. Preferably, the composition is applied to clean hair.

According to one particular embodiment of the invention, the application of the composition may be followed by drying at ambient temperature or at a temperature above 40° C.

The drying may be performed immediately after the application or after a leave-on time that may range from 1 minute to 30 minutes.

The present invention also relates to the use of the composition defined above, sprayed from the aerosol device according to the invention, for shaping the hair and/or retaining the hairstyle, and in particular for giving the hairstyle volume.

The examples that follow serve to illustrate the invention.

EXAMPLES

In the examples that follow, all the amounts are indicated as weight percentage of product as active materials relative to the total weight of the composition.

Example 1

The following compositions according to the invention were prepared from the compounds indicated in the table below.

| Composition | A | B | C | D | E | F |
|---|---|---|---|---|---|---|
| Calcium carbonate[1] | 5 | 2 | 1 | 1 | 0.8 | 3 |
| Polyvinylcaprolactam[2] | 1.2 | 2 | — | — | — | — |
| Vinylpyrrolidone/vinyl acetate copolymer[3] | — | — | — | 6 | — | — |
| Polyquaternium-4[4] | — | — | 2 | — | — | — |
| Vinylamine/vinylformamide copolymer[5] | — | — | — | — | 7.7 | — |
| AMP-acrylates/allyl methacrylate copolymer[6] | — | — | — | — | — | 7.5 |
| Hydroxyethylcellulose[7] | — | 0.1 | — | — | 0.15 | — |
| Scleroglucan gum[8] | 0.4 | — | — | 0.3 | — | 0.22 |
| Polyoxyethylenated (PEG-40) and hydrogenated castor oil | 0.8 | 0.5 | 0.7 | 0.6 | 0.7 | 0.6 |
| Cetyltrimethylammonium chloride | — | — | 0.05 | 0.06 | 0.08 | — |
| Laureth-4 | 1 | — | 0.5 | — | 0.2 | 0.4 |
| Cocamidopropyl betaine | — | — | — | 0.2 | — | — |
| Sodium lauryl sulfate | — | 0.35 | — | — | — | 0.07 |
| Propylene glycol | — | 3 | — | — | 2 | — |
| Fragrance | 0.3 | 0.3 | 0.3 | 0.3 | 0.3 | 0.3 |
| Preservative | 0.3 | 0.3 | 0.3 | 0.3 | 0.3 | 0.3 |
| Ethanol | — | — | — | 3 | — | — |
| Isobutane/Butane/Propane[9] | 10 | 4.5 | 5 | 4.5 | 5 | 6 |
| Dimethyl ether | — | — | — | 1.5 | — | — |
| 1,1-Difluoroethane[10] | — | 1.5 | — | — | — | — |
| Water qs | 100 | 100 | 100 | 100 | 100 | 100 |

[1]Sold under the trade name OMYACARE S 60-AV by the company Omya,
[2]Sold under the trade name LUVISKOL PLUS by the company BASF,
[3]Sold under the trade name LUVISKOL VA 64 W by the company BASF,
[4]Sold under the trade name CELQUAT LOR by the company Akzo Nobel,
[5]Sold under the trade name LUVIQUAT 9030 by the company BASF,
[6]Sold under the trade name FIXATE G-100L PR POLYMER by the company Lubrizol,
[7]Sold under the trade name NATROSOL 250 HHR PC by the company Ashland,
[8]Sold under the trade name AMIGEL by the company Alban Muller,
[9]Sold under the trade name PROPEL 45 by the company Repsol,
[10]Sold under the trade name DYMEL 152 A by the company DuPont.

Each composition was then introduced into an aerosol device which comprises a 210 ml aluminium can equipped with a foam-propelling device comprising a valve, in particular a P14180 Precision valve, and a foam diffuser, in particular a DMPR190 Precision diffuser, the valve and the diffuser being sold by the company Valve Precision. The compositions are applied in the form of mousses to a head of hair.

After application of the mousse, it is noted that the fibres are given volume, texturization and body while a natural appearance of the head of hair is maintained, without any helmet effect.

Example 2

A composition of a commercial product (composition H) was compared to a composition according to the invention (composition G).

| | Composition | |
|---|---|---|
| | G (Invention) | H (comparative) |
| Calcium carbonate[1] | 5.23 | — |
| Polyquaternium-4 [2] | 1.43 | 1.41 |
| Scleroglucan gum[3] | 0.29 | — |
| Polyoxyethylenated (PEG-40) and hydrogenated castor oil | 0.86 | 0.85 |
| Cetyltrimethylammonium chloride | 0.05 | 0.05 |
| Laureth-4 | 0.38 | 0.38 |
| Fragrance | 0.29 | 0.19 |
| Phenoxyethanol | 0.67 | 0.47 |
| Preservative | qs | qs |
| Propylene glycol | 2.38 | 2.35 |

-continued

|  | Composition | |
| --- | --- | --- |
|  | G (Invention) | H (comparative) |
| Isobutane/Butane/Propane [4] | 5 | 6 |
| Water qs | 100 | 100 |

[1] Sold under the trade name OMYACARE S 60-AV by the company Omya,
[2] Sold under the trade name CELQUAT LOR by the company Akzo Nobel,
[3] Sold under the trade name AMIGEL by the company Alban Muller,
[4] Sold under the trade name PROPEL 45 by the company Repsol.

Each composition was then introduced into an aerosol device which comprises a 210 ml aluminium can equipped with a foam-propelling device comprising a valve, in particular a P14180 Precision valve, and a foam diffuser, in particular a DMPR190 Precision diffuser, the valve and the diffuser being sold by the company Valve Precision.

2 g of each of the mousses was applied to wet locks per half head. This application is carried out on 6 heads for each of the compositions.

The qualities of use on application and the cosmetic properties conferred on the hair after blow-drying were then evaluated. It emerges therefrom:
   that, on application, greater texturization is obtained with composition G according to the invention, and
   that, after blow-drying, the hair treated with composition G according to the invention exhibits greater texturization and greater mass.

The invention claimed is:

1. An aerosol device which contains a composition, said composition comprising:
   (i) calcium carbonate,
   (ii) at least one fixing polymer chosen from AMP-acrylates/allyl methacrylate copolymer, vinyllactam homopolymers, vinyllactam copolymers, vinylamine/vinylformamide copolymers, polyquaternium-4, or mixtures thereof,
   (iii) at least one surfactant chosen from anionic, cationic, non-ionic, amphoteric, or zwitterionic surfactants, or mixtures thereof,
   (iv) water, and
   (v) at least one propellant, present in an amount of less than about 20% by weight, relative to the total weight of the composition,
   wherein the weight ratio of the total amount of the at least one fixing polymer to the total amount of the at least one surfactant ranges from 0.5 to 8.

2. The aerosol device according to claim 1, wherein the calcium carbonate is in the form of a powder comprising particles which have a mean diameter ranging from about 2 µm to about 50 µm.

3. The aerosol device according to claim 1, wherein the calcium carbonate is present in an amount ranging from about 0.1% to about 15% by weight, relative to the total weight of the composition.

4. The aerosol device according to claim 1, wherein the at least one fixing polymer is present in an amount ranging from about 0.1% to about 15% by weight, relative to the total weight of the composition.

5. The aerosol device according to claim 1, wherein the at least one surfactant is chosen from $(C_6$-$C_{24})$alkyl sulfates; $(C_6$-$C_{24})$alkyl ether sulfates comprising from 2 to 50 ethylene oxide units; polyethoxylated $C_8$-$C_{18}$ alcohols, the number of ethylene oxide groups ranging from 2 to 50; vegetable oils, which are optionally hydrogenated; polyethoxylated vegetable oils; $(C_8$-$C_{20})$alkylbetaines; $(C_8$-$C_{20})$alkylamido $(C_1$-$C_6)$alkylbetaines; $(C_8$-$C_{29})$alkyl amphodiacetates; cetyltrimethylammonium salts; or mixtures thereof.

6. The aerosol device according to claim 1, wherein the at least one surfactant is present in an amount ranging from about 0.05% to about 10% by weight, relative to the total weight of the composition.

7. The aerosol device according to claim 1, wherein the at least one propellant is chosen from dimethyl ether; 1,1-difluoroethane; $C_3$-$C_5$ alkanes; or mixtures thereof.

8. The aerosol device according to claim 1, wherein the at least one propellant is present in an amount of less than about 15% by weight, relative to the total weight of the composition.

9. The aerosol device according to claim 1, wherein the water is present in an amount of more than about 5% by weight, relative to the total weight of the composition.

10. The aerosol device according to claim 1, wherein the composition further comprises at least one thickening polymer.

11. The aerosol device according to claim 10, wherein the at least one thickening polymer is chosen from polysaccharides, scleroglucan gums, or mixtures thereof.

12. The aerosol device according to claim 1, further comprising at least one additive chosen from silicone derivatives in soluble forms, silicone derivatives in dispersed forms, silicone derivatives in micro-dispersed forms; solvents; clays; silica; plasticizers; anti-agglomerating agents; protective screening agents; acids; bases; nacres; flakes; fragrances; permanent dyes; temporary dyes; treating active agents, or mixtures thereof.

13. A method for shaping the hair and/or retaining the hairstyle, the method comprising:
   applying, to dry or wet hair, a composition sprayed from an aerosol device, the composition comprising:
   (i) calcium carbonate,
   (ii) at least one fixing polymer chosen from AMP-acrylates/allyl methacrylate copolymer, vinyllactam homopolymers, vinyllactam copolymers, vinylamine/vinylformamide copolymers, polyquaternium-4, or mixtures thereof,
   (iii) at least one surfactant chosen from anionic, cationic, non-ionic, amphoteric, or zwitterionic surfactants, or mixtures thereof,
   (iv) water, and
   (v) at least one propellant, present in an amount of less than about 20% by weight, relative to the total weight of the composition,
   wherein the weight ratio of the total amount of the at least one fixing polymer to the total amount of the at least one surfactant ranges from 0.5 to 8; and
   optionally rinsing the composition from the hair after an optional leave-on time and/or after optional drying.

* * * * *

UNITED STATES PATENT AND TRADEMARK OFFICE
CERTIFICATE OF CORRECTION

| | | |
|---|---|---|
| PATENT NO. | : 11,154,466 B2 | Page 1 of 1 |
| APPLICATION NO. | : 15/322771 | |
| DATED | : October 26, 2021 | |
| INVENTOR(S) | : Jonathan Gawtrey et al. | |

It is certified that error appears in the above-identified patent and that said Letters Patent is hereby corrected as shown below:

In the Claims

Column 26, Claim 5, Line 8, please change "(C8-C29)" to -- C8-C20 --.

Signed and Sealed this
Twenty-eighth Day of June, 2022

Katherine Kelly Vidal
*Director of the United States Patent and Trademark Office*